United States Patent [19]

Surugue nee Lasnier et al.

[11] Patent Number: 4,898,572
[45] Date of Patent: Feb. 6, 1990

[54] AUTOTRANSFUSER

[75] Inventors: Evelyne Surugue nee Lasnier; Hubert Lasnier, both of Creteil; Phillipe Perovitch, Merignac, all of France

[73] Assignee: Futur-Quotidien S.A., Merignac, France

[21] Appl. No.: 127,053

[22] Filed: Dec. 1, 1987

[51] Int. Cl.⁴ ............................................. A61M 37/00
[52] U.S. Cl. ....................................................... 604/4
[58] Field of Search ................ 128/DIG. 3, DIG. 12; 604/4-6, 27, 32, 35, 49-53, 317-320, 406, 410, 416; 210/497.3, 416.1, 339, 335, 323.1, 252, 255, 258

[56] References Cited

U.S. PATENT DOCUMENTS

| | | | |
|---|---|---|---|
| 2,847,007 | 8/1958 | Fox | 604/406 |
| 3,221,741 | 12/1965 | Le Veen | 604/416 |
| 3,585,995 | 6/1971 | Perkins et al. | 604/4 |
| 3,827,562 | 8/1974 | Esmond | 604/406 |
| 4,006,745 | 2/1977 | Sorenson et al. | 604/4 |
| 4,014,329 | 3/1977 | Welch et al. | 604/4 |
| 4,033,345 | 7/1977 | Sorenson et al. | 604/4 |
| 4,157,965 | 6/1979 | Raible | 210/335 |
| 4,170,056 | 10/1979 | Meyst et al. | 604/406 |
| 4,440,723 | 4/1984 | Gordon | 128/DIG. 3 |
| 4,443,220 | 4/1984 | Hauer et al. | 604/4 |
| 4,772,256 | 9/1988 | Lane et al. | 604/4 |

Primary Examiner—C. Fred Rosenbaum
Attorney, Agent, or Firm—Fisher, Christen & Sabol

[57] ABSTRACT

An autotransfuser device for removing blood from a patient and returning the blood to the patient includes a collection bag suspended in an air jacket. A valve is provided in the device to selectively apply a negative pressure to the air jacket and the interior of the collection bag to draw the blood from the patient. The valve is subsequently rotated to apply a positive pressure to the air jacket and the outside of the bag to compress the bag and cause the blood to be returned to the patient. A plurality of filter members are provided in a collection chamber to remove blood clots and undesirable solids. A source of an anticoagulant may be provided in the collection chamber and in the collection bag.

17 Claims, 6 Drawing Sheets

AUTOTRANSFUSER

The present invention relates to a device for recovering and reinjecting blood, more particularly in order to compensate haemorrhages in patients or seriously injured persons in situations where a surgical operation is serious or long, or difficult, for example when it is impossible to have blood of the same group rapidly available for transfusion.

In the event of surgical operations carried out under difficult conditions, particularly in the case of catastrophes such as earthquakes, railway accidents, industrial catastrophes, etc. . . . , the large quantity of blood necessary for transfusion for the haemorrhagic injured is wanting.

The problems arising in the event of catastrophes are also encountered in the case of surgery of the war-wounded (which is always carried out on or near the battle-field), due to the difficulties in the supply of blood, in quality and in quantity, necessary for the transfusions.

It is also known that blood transfusion involves the risk of injecting blood carrying germs or viruses coming from the donor, which have been poorly revealed.

It is therefore an object of the present invention to provide a device for recovering and reinjecting blood adapted to overcome the drawbacks set forth hereinabove and generally to enable a haemorrhaging patient or injured person immediately to recover some of his blood, under good conditions of safety.

The present invention relates to a device for recovering and reinjecting into a patient's organism his own blood in order to compensate a haemoerrhage, of the type comprising sterile means for recovering the blood by suction, adapted to be positioned in the immediate proximity of the point of rupture of the vessels, filtering means for eliminating the coagulated blood platelets, means for injecting anti-coagulant products into the collected blood and means for circulating the blood allowing, on the one hand, suction thereof and, on the other hand, reinjection thereof via a tube connected to transfusion means into the patient's blood circulatory system, said device characterized in that the means for recovery by suction are connected by a tube to a first filtration chamber adapted to collect the blood, the chamber being provided with superposed filtering beds, in vacuo, the base of the filtration chamber being to that end adapted to be placed in communication with a source of depression, and said filtration chamber is in communication at its top with a source of anti-coagulant products, allowing dispersion of said anti-coagulant products in the form of a fog adapted to fill the gaseous phase of said filtration chamber above and upstream of the filtering beds, the filtration chamber being in communication by its base with a second chamber or collecting and storage chamber located beneath the filtration chamber, the collecting and storage chamber thus being adapted to collect the blood flowing by gravity from the filtration chamber, said collecting and storage chamber comprising a second reserve of anti-coagulant agents in communication with said collecting and storage chamber by dispersion means allowing diffusion of said agents into the blood stored in said chamber, the base of the collecting and storage chamber communicating by a lower outlet tube with means for transfusion back into the patient's blood circulatory system via second filtration means.

The means for circulating the blood are advantageously constituted, on the one hand, by suction means, particularly a source of depression and, on the other hand, by delivery means comprising in particular at least one source of excess pressure and the device comprises a multi-way valve adapted to ensure, alternately, the connection of the assembly of the two filtration and collecting chambers with the source of depression for the purpose of recovering the blood, or the connection of the collecting chamber with the delivery means such as a source of excess pressure for the purpose of facilitating reinjection of the blood into the patient's circulatory system.

The invention will be more readily understood on reading the following description with reference to the accompanying drawings, in which.

Referring now to the drawings, the blood is taken and collected by suction at the wound by a sound or known device (not shown) terminating in a supple tube connected by the tube section 31 to a filtration chamber formed by the vessel 2. This vessel 2 is truncated, with downwardly decreasing section and generatrix (or side wall) 4 with weak inclination. The bottom 5 of the vessel is in the form of a funnel, terminating at its centre in a central passage 6 for connection to the collecting and storage chamber formed by the supple bag 25 within the vessel 18.

The filtration chamber 2 comprises a series of superposed filtering beds or cloths 9, 9a, 9b, 9c, 9d generally in the form of a cone with upwardly directed apex, the upper cloth 9 comprising an upwardly open truncated periphery (with a diametrical section in W-form). The purpose of the arrangement of the conical filters 9a to 9c with their apices oriented upwardly is to offer the filtered matter a larger surface of deposit on the periphery of the filters.

The upper cloth 9 is perforated uniformly over the whole of its surface (cf. pores 12) which is covered with vertical points 11. The large "debris" is thus retained by the "forest of points" and the blood can flow between the points 11 and through the pores between the points 11 and through the pores 12. The filtering cloth 9 has mesh with a width of at least 1 mm diameter, with the result that, on a surface of 2 mm$^2$, there is always at least one orifice of 1 mm diameter and 3 to 4 points which surround it. These points present an irregular relief, with roughness, enabling the "débris" which passes nearby to catch thereon more easily. The relief thereof is more irregular at the top than at the base.

The mesh size of the filtering cloths 9a to 9c is finer with respect to that of cloth 9, and is progressively finer from cloth 9a to cloth 9c.

The cloths are each mounted on a peripheral ring and the average diameter of the rings decreases in such an order that the filtering cloths 9 and 9a to 9c can be positioned by force-fit inside the conical vessel 2 and against the inner face of wall 4 thereof: in this way, each filter can occupy only a well defined place, corresponding to the order of filtering provided, and no risk of error is possible in the assembly of the filters.

Figure 4:
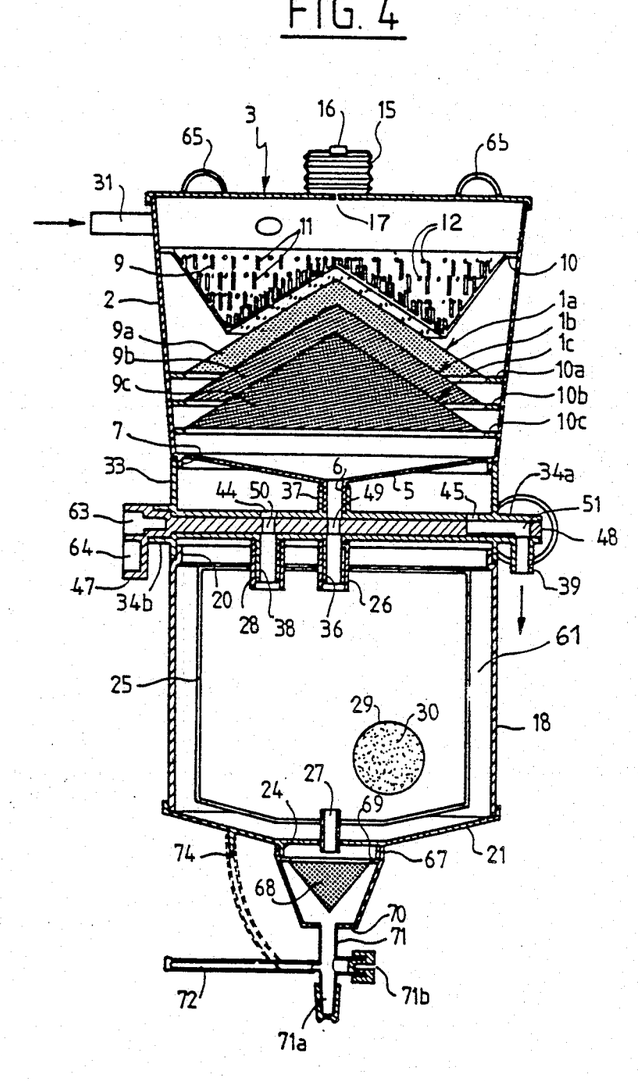
FIG. 4 is a view in vertical axial section of the device shown in FIG. 2.
Figure 5:
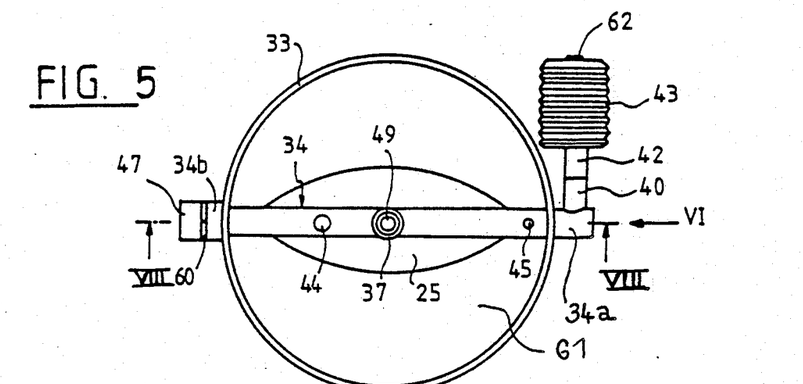
FIG. 5 is a plan view of the suction/delivery assembly of the device.
Figure 6:
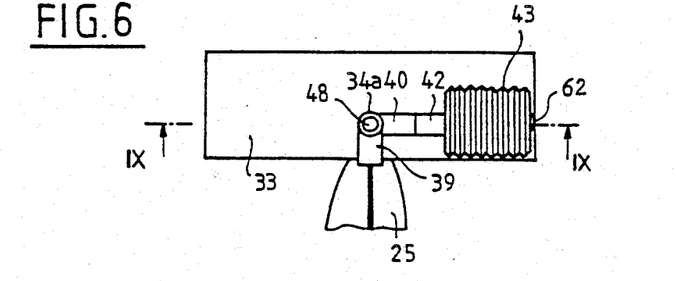
FIG. 6 is a view in elevation, in the direction of VI and with parts torn away, of the suction/delivery assembly illustrated in FIG. 5.

A lid 3 fits on the vessel 2 to close it. It is fixed to this vessel by adhesion. In the upper part of the lid 3 is disposed a bellows 15 (cf. also FIGS. 2 and 4) adapted to be filled with an anti-coagulant with the aid of a syringe and needle (not shown) by injection through an elastomer stopper 16. This bellows/reservoir allows vaporization of said anti-coagulant before and during suction of the operative blood; to that end, the bellows 15 for vaporization of the anti-coagulant products communicates with a spray nozzle 17 pierced in the lid 3 in the axis of the bellows.

This lid is advantageously provided with handles or eyelets 65 for suspension, which enable the device according to the invention to be maintained in vertical position to ensure delivery by gravity of the sucked and collected blood.

The collecting and storage chamber formed by the bag 25 is located in the vessel 18 closed at its base by a bottom 21 substantially in the form of a funnel and which presents a central horizontal portion (or disc) 22 pierced with an axial orifice 23.

The vessel 18 contains a bag 25 made of supple plastics material, for example of Triothyltrimethylate (TOTM), which allows oxygen and CO to pass through and which is manufactured by the U.S. firm CUTTER.

The bag 25 constituting the blood collecting chamber is fitted with a plurality of connecting pieces 26 to 28 whose function will be specified hereinbelow. This bag 25 contains a pouch 30, for example spherical in shape, whose wall is made of a supple, cellulated and porous plastics material, or of porous colloids, and which is filled with an anti-coagulant substance which is released into the bag 25 as described hereinafter. A substantially cylindrical belt 33 fits between the upper vessel 2 and the lower vessel 18 and connects them together.

The belt 33 supports in diametral position a tubular piece 34 forming a body for receiving the key 48 constituting with the body a multi-way valve.

Figure 7:
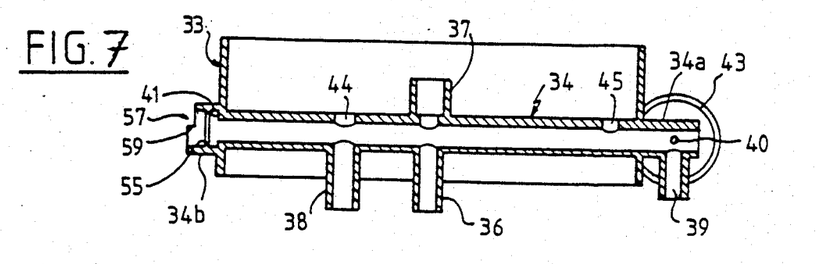
FIG. 7 is a view in vertical axial section of the suction/delivery assembly according to the invention, as shown in FIG. 1, the body of the multi-way valve being bereft of its control key according to the invention.
Figure 8:
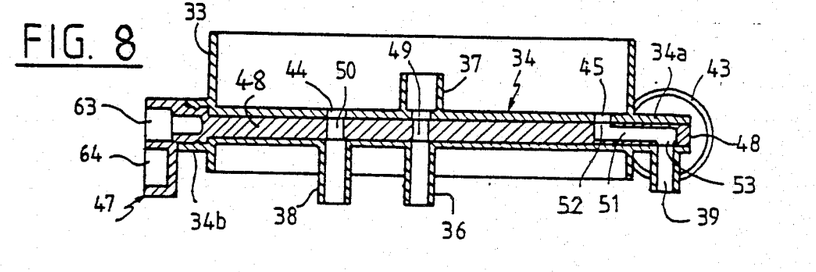
FIG. 8 is a view in vertical axial section along the plane VIII of the suction/delivery assembly illustrated in FIG. 7, showing the key of the valve in position for suction of the blood.
Figure 15:
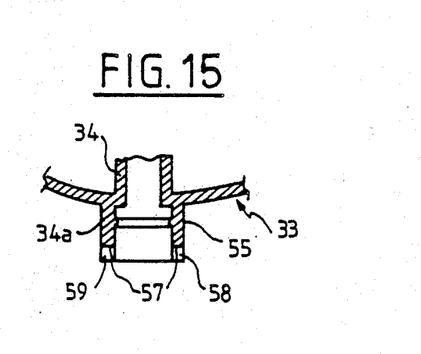
FIG. 15 is a view on a larger scale of a detail of that portion of the valve body cooperating with the handle of the control tap.

The body 34 extends outwardly of the belt 33 on either side of the vertical axis of the device, so as to define a portion 34a with the same inner and outer diameters and a portion 34b whose inner and outer diameters are larger than that of the tubular piece 34 so as to define a shoulder 41 (cf. FIGS. 7 and 15) forming stop for the key 48. The valve body comprises a plurality of ways 36 to 40, of which ways 36 to 39 are contained in a vertical plane passing through the axis of the body 34 and are perpendicular to this axis, whilst way 40 is contained in a horizontal plane also passing through the axis of said body, it too being perpendicular to this axis.

Ways 36 and 37 are colinear and receive by fit the likewise colinear channels 6 and 26 coming respectively from the filtration chamber 2 and the collecting chamber 25.

A way 38 of the body also receives by engagement the channel 28 coming from the collecting chamber. Ways 39 and 40 are located outside the belt 33 and are borne by the outer portion 34a of the body 34. Way 39, which is directed downwardly, is connected to a source of vacuum 39a, whilst way 40 (which is directed horizontally and is at right angles with respect to way 39) receives the tube 42 of a bellows 43.

In the wall of body 34 are also made three orifices 44 to 46, of which orifice 44 is arranged in position diametrically opposite with respect to way 38.

Key 48 mounted to rotate in body 34, comprises a handle 47 and it is made of a plastics material having self-lubricating properties, such as polyethylene with high molecular mass or the like, and engaged with slight friction in body 34; like the key, the latter presents a uniform cylindrical section, constant from one end to the other, in order to ensure perfect tightness of the circuits which will be described hereinafter. In key 48 are made two transverse channels 50 and 49 adapted to communicate with way 38 and orifice 44 and, respectively, the diametrically opposite ways 36, 37 of body 34.

In addition, in key 48 is made an axial channel 51, blind at both ends and having access to the surface of the key by two orifices 52, 53 adapted to communicate either with way 39 and orifice 45, or with bellows 43 and orifice 46 mentioned above: therefore, in position of assembly, the channel 51 comprises two portions which are located on either side of the belt 33.

Figure 9:
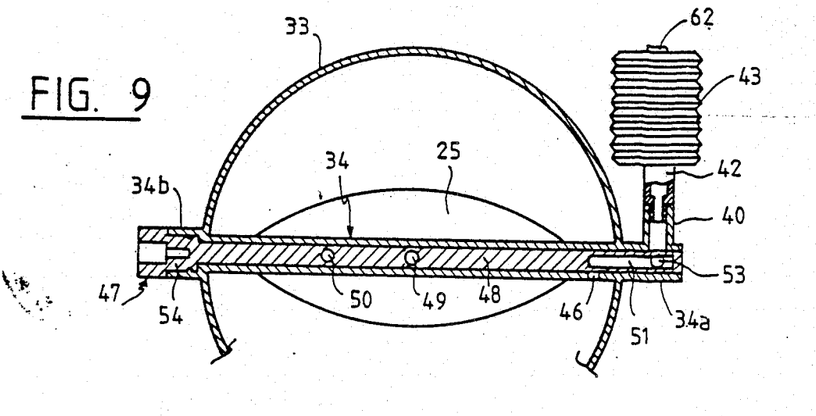
FIG. 9 is a view in horizontal section along plane IX of the suction/delivery assembly illustrated in FIG. 8, showing the control tap also in position of suction.
Figure 10:
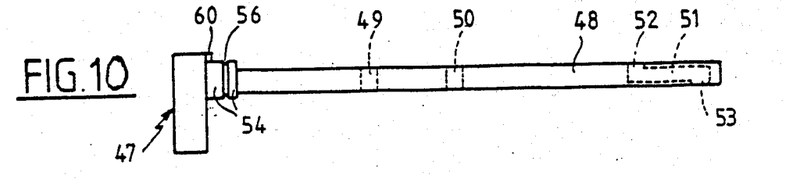
FIG. 10 is a view in elevation of the key of the multi-way valve shown in position of suction corresponding to FIG. 9.
Figure 11:
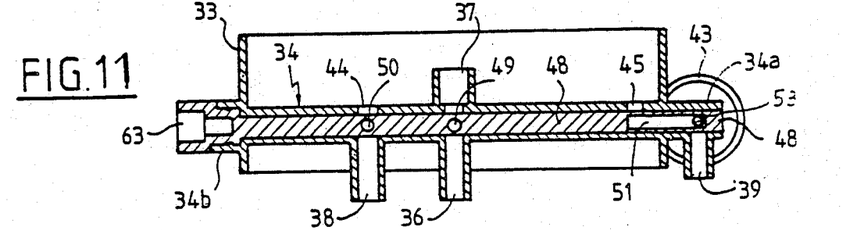
FIG. 11 is a view in vertical axial section of the suction/delivery assembly in which the key of the valve is in position for compression of the bag for collecting the blood, and therefore of delivery of the latter.
Figure 12:
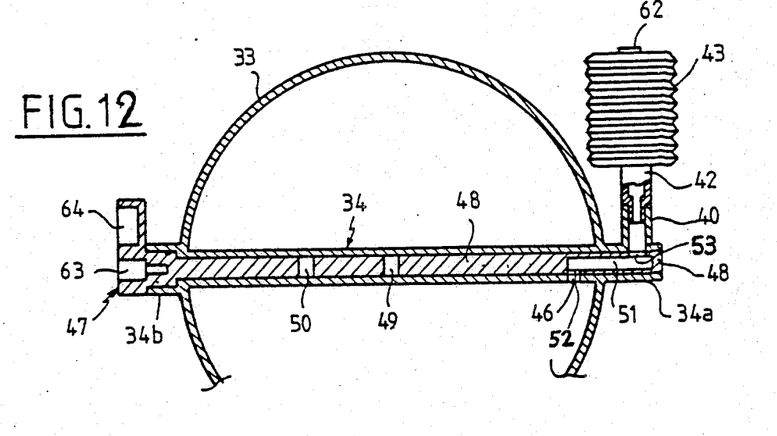
FIG. 12 is a view in horizontal section of the suction/delivery assembly, the key being in the same position as that shown in FIG. 3.
Figure 13:
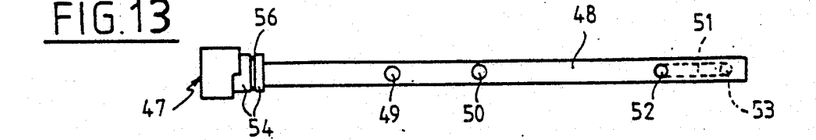
FIG. 13 is a view in elevation of the key shown in the position corresponding to FIG. 11.
Figure 14:
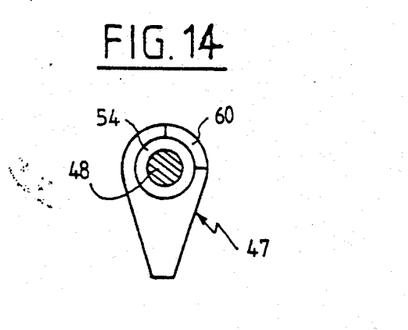
FIG. 14 is a front view on a larger scale of the handle of the multi-way valve.

The handle 47 for manoeuvring the key 48 comprises recesses 63 and 64 for lightening purposes and is perpendicular to key 48 to which it is connected by a cylindrical portion 54 adapted to fit in portion 34b of the tubular body 34 by clipping an annular rib 55 (cf. FIGS. 9 and 17) thereof in an annular groove 56 (cf. FIGS. 12 and 15) in the portion 54 mentioned above for connecting handle 47 to key 48.

At the end of portion 34b there is made a semi-circular groove 57 (cf. FIGS. 9 and 17) defining two diametrically opposite shoulders 58 and 59 (cf. FIG. 17) in portion 34b. The cylindrical portion 54 mentioned above comprises an arcuate catch 60, defined by an arc of 90°, which is adapted to rotate in the semi-circular groove 57 and to come into abutment either against shoulder 58 or against shoulder 59 by rotation of the handle 47 through a quarter turn.

Figure 3:
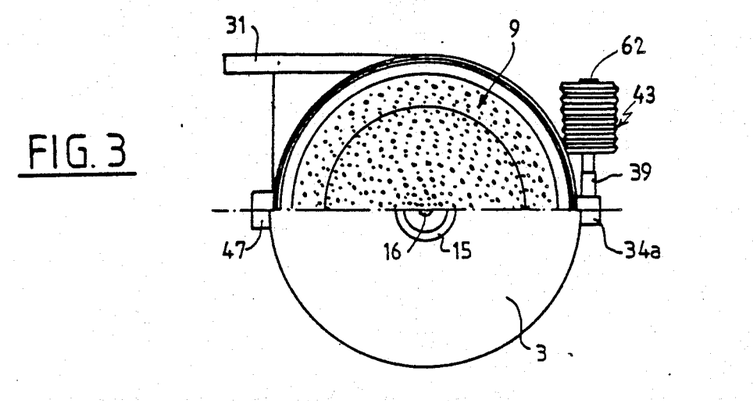
FIG. 3 is a plan view, with parts torn away, of the device shown in FIG. 2.

When catch 60 of handle 47 is in abutment against the shoulder 58, namely when this handle is directed vertically downwardly, as appearing in FIG. 3, the first way 37 communicates with the second way through the internal channel 49 of the key; the third way 45 communicates through the internal channel 51 of the key with a sixth way 39 (leading to the source of depression) and the fourth way 44 communicates through internal channel 50 with a fifth way 38.

Ways 44 and 45 communicate together via the air jacket 61 defined between the inner surfaces of vessel 18 and of belt 33, the bottom 5 of vessel 2 as well as the outer surfaces of bag 25. It is clear that, under these conditions, key 48 is in position of suction, which makes it possible to evacuate the air contained in bag 25 through way 38 forming breather and, consequently, to create a depression in the bag, and therefore in vessel 2, via the passage defined by channel 50 of the key and ways 36 and 37 of body 34.

This depression is also transmitted to the 35 suction sound of cannula via tube 31 of vessel 2.

Way 38 is advantageously provided with an anti-bacterial filter of conventional type (not shown), whose porosity is of 0.10 to 0.25 microns.

The depression created in jacket 61 distends the membrane 29 of the pouch 30 filled with anti-coagulant substance and contained in bag 25, thus enlarging the pores of the membrane and causing its structure to give way, with the result that the anti-coagulant liquid is released and mixes with the blood. In any case, spraying by spray nozzle of the anti-coagulant substances contained in the bellows 15 (cf. FIGS. 1 and 4), causes said substances to spread over the inner walls of the device, particularly the filters where they mix with the blood.

When catch 60 of handle 47 is in abutment against the shoulder 58, namely when this handle is horizontal, channels 49 and 50 of the key as well as orifice 53 of the blind channel 51, made in the key, are obturated by the wall of the body 34, whilst the orifice 52 of the blind channel 51 is in communication with the seventh way 46 of the body 34. Under these conditions, the bellows 43 is in communication with said jacket 61 in which air may therefore be blown in order to create an excess pressure in this jacket and therefore to compress the bag 25 filled with blood so as to allow transfusion towards the patient's body. The bellows 43 is removable and locks easily in the connecting piece 40 of piece 34 thanks to the presence of locking grooves made over a ¼ turn (not shown, as this locking system is known to the man skilled in the art), in its connecting tube 42, tightness being obtained by means of a supple seal.

An air admission valve 62 allows air to enter when the bellows 43 is actuated. If necessary, this bellows may be unscrewed to lower the pressure in the air jacket 61 when the flowrate is relatively high. The position in which the key is located under these conditions is a position thus ensuring improved delivery of the blood sucked and collected in the bag 25, towards the patient.

The base of vessel 8 comprises a truncated filtration basin 66 which extends at the upper bottom, of larger diameter, in a substantially cylindrical ring 67 adapted to fit around the annular rib 24 projecting from the central, horizontal, lower portion of the bottom 21 of the vessel 18 containing the bag 25 for collecting blood. The lower connecting piece 27 of the latter is fitted in the central orifice 23 made in bottom 21. The necessary tightness between vessel 18 and the basin 66 as well as between the connecting piece 27 and the bottom 21 is obtained by adhesion.

Within the basin 66 is housed a filter composed of a conical element 68 made of textile of plastics material, of which the meshes present a diameter of 75 $\mu$m and of which the apex is oriented downwardly, in the direction of the truncated basin 66, and which is fixed, by adhesion or welding, to a thin cylindrical ring 69 whose outer diameter is substantially equal to the inner diameter of the ring 67: in this way, the filter is automatically positioned in the upper part of the basin 66. This basin 66 is also a means allowing, in addition to the filtration of the blood before passage thereof in the transfusion line, a first release of the air bubbles which might be conveyed with the blood, it being understood that the chamber of the transfuser connected to the apparatus will also perform this role thereafter, and that a bubble trap may then be placed on the conventional transfusion line, as an additional precaution.

A tube 71, with two ways or connecting pieces 71a and 71b, projects downwardly from the base 70 of the basin 66. Connecting piece 71a allows the device according to the invention to be connected to a conventional transfuser, namely to a conventional transfusion tube known to the man skilled in the art (not shown). Connecting piece 71b, which is of type known under the Trademark "Luer-lock", allows connection to a roller pump (likewise not shown, as it is known to the man skilled in the art) intended to mobilize the blood transferred towards the patient.

Figure 1:
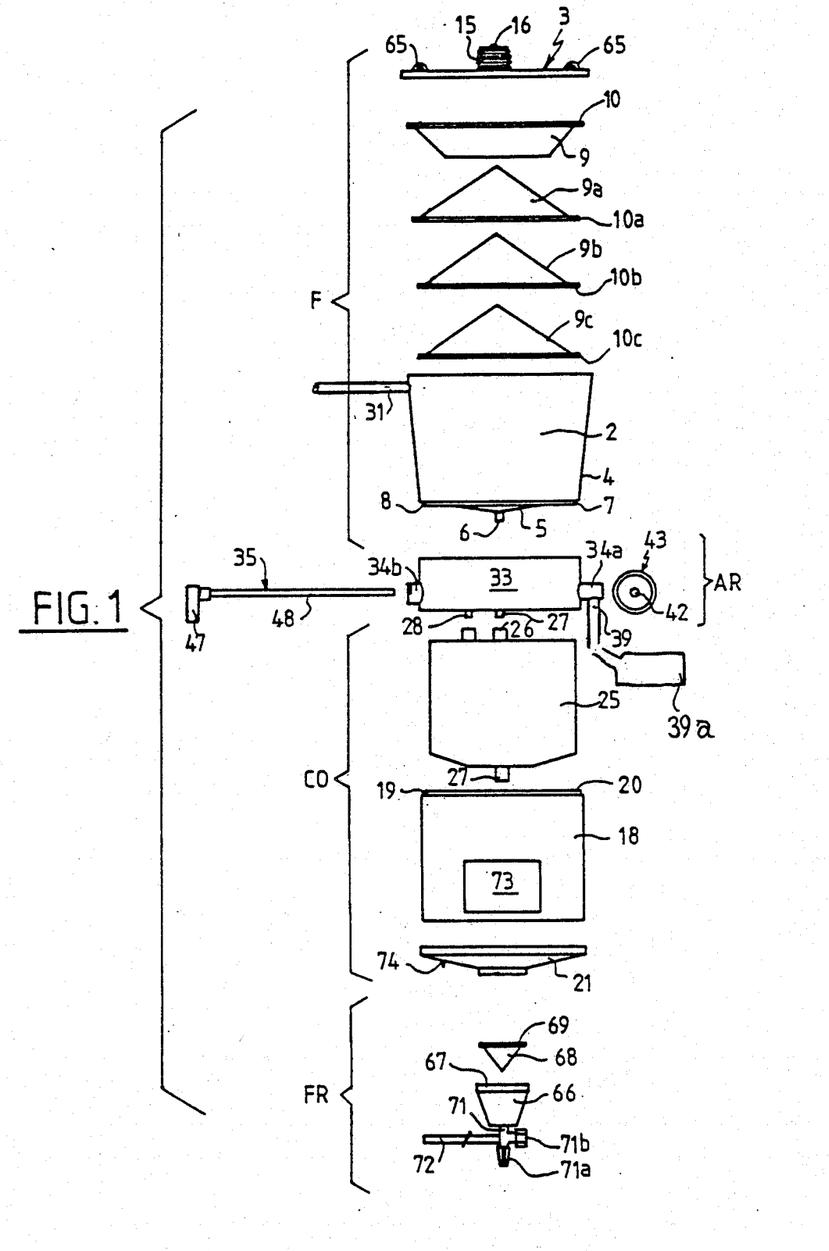
FIG. 1 is an exploded view of the device according to the invention.
Figure 2:
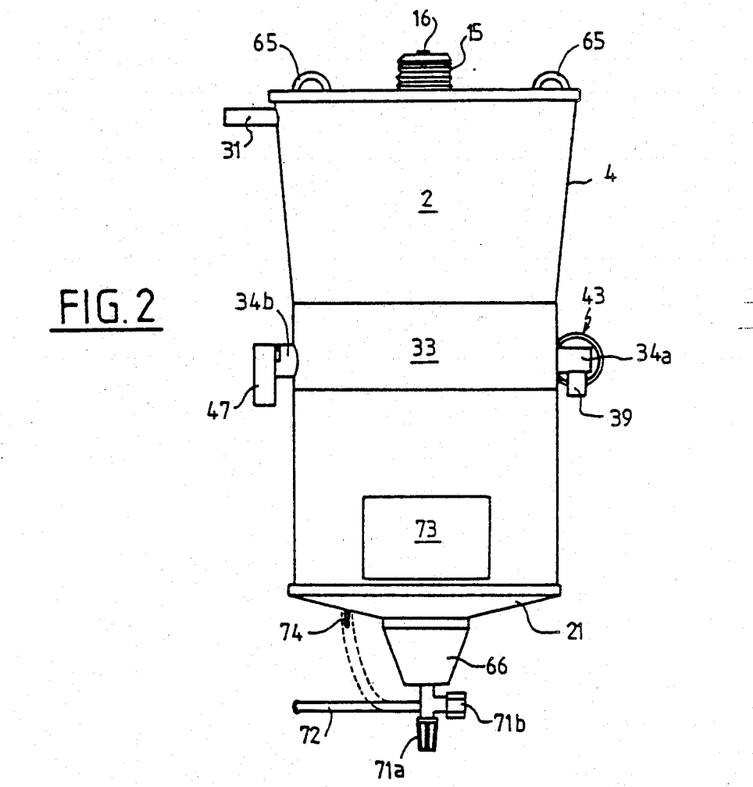
FIG. 2 is a view in vertical elevation of the device according to the invention, with the component parts illustrated in FIG. 1 assembled together.

Tube 71 is also provided with a capillary tube 72 rendered blind at its free end, for example by crimping, and adapted to take blood from the collecting bag 25 necessary for checking the patient's blood group; this is effected by cutting the crimped end of the capillary tube 72 and by applying some drops of blood on test plates which may be stuck on an identifying label, as schematically illustrated in FIGS. 1 and 2 and designated by reference 73. These test plates may advantageously be protected by a fine film of plastics material which guarantees single use thereof.

Once the blood group has been checked, the capillary tube 72 may be closed again by engaging it on a point 74 which projects downwardly from the bottom 21 of the vessel 18, and which serves as stopper. The diameter of this plastic capillary tube makes it possible to introduce thereinto the standardized endpiece of a sterile syringe in order to remove, in addition to the blood necessary for testing the blood group, larger quantities of blood for haemocultures, checking of the coagulation factors, coagulability, etc. . . .

The auto-transfusion device according to the invention is entirely sterile internally and externally and may advantageously be delivered in a hermetic packing. Made of bio-compatible plastics materials, it serves only for one collection of a quantity of blood not exceeding 500 to 800 cc (single-use).

The device according to the invention does not present drawbacks for the patients, if consideration is given to the following:

the anti-coagulant products employed therein have been used for decades; in particular, heparin which is used in the device and passes in the patient's circulation during transfusion, may be rapidly and efficiently neutralized as to its systemic anti-coagulant effects, thanks to the use of injectable protamine;

all the plastics materials used are highly bio-compatible and, apart from the cold storage (for which the bag present in the device is usually used), the time of contact of the blood with these materials is short;

the filters with which the auto-transfusion device is fitted guarantee against the passage of aggregates or foreign bodies or of particles constituted during the subsequent transfusion of the collected blood;

the anti-bacterial filter of the breather is a barrier to the bacterial contamination of the air; it is known for a fact that, despite all the precautions taken in the operating theatre, contamination is always present, justifying for all these patients appropriate preventive antibiotic treatments depending on the nature of the germs likely to have contaminated the patients. The present device is all the more advantageous as it enables the patient to recover part of his natural defences present in the circulating blood and which would otherwise be lost.

The invention makes it possible to produce a compact auto-transfusion unit of small dimensions, made of haemocompatible synthetic matter and even a material with anti-coagulant properties (containing heparins); it is of moderate cost price allowing single use with complete safety.

The tube connecting the suction means such as the blood suction nozzle, to the filtration chamber, is itself connected, in the vicinity of said suction nozzle, to a source of an active product in the liquid state adapted thus to be injected into said tube immediately after the blood introduction phase.

The source of liquid active products is constituted by an auxiliary tube opening via a connection into the tube mentioned hereinbefore immediately after the suction nozzle and said auxiliary tube being adapted to be connected by its opposite end to a reserve of active products in the liquid state.

These active products include the following groups:
(a) anti-coagulant products such as heparin citrate;
(b) isotonic liquids such as an isotonic saline solution;
(c) aqueous emulsions of macromolecules of the DEXTRAN type;
(d) artificial liquids ensuring transfer of oxygen into the organism and constituting artificial blood.

At least one of the chambers in which the blood circulates in its extra-corporal circuit, comprises on an appropriate support, preferably of granular nature, products with bactericidal and bacteriostatic action constituted by compounds comprising modules of oxidizing iodine, and in particular, said compounds incorporating molecules of oxidizing iodine and with bacteriostatic or bactericidal action, are adsorbed or grafted on a support constituted by granules of purified vegetable carbon.

The same compounds including oxidizing iodine may also be used to constitute a filtration bed to ensure purification of the air in communication with the said blood collecting chamber.

What is claimed is:

1. A device for recovering and re-injecting blood into a patient comprising:
   (a) suction means for recovering the blood;
   (b) a first chamber forming a filtering chamber connected to said suction means;
   (c) a plurality of filtering beds inside said filtering chamber;
   (d) a source of negative pressure and a source of positive pressure; (e) a first source of anticoagulant products connected to said filtering chamber;
   (f) a second chamber forming a blood collecting chamber, located beneath the filtering chamber to receive the blood by gravity from the filtering chamber;
   (g) a second source of anti-coagulant products inside said collecting chamber;
   (h) second filtration means at the base of said collecting chamber;
   (i) means for back-transfusion of blood into the patient's circulatory system from said collecting chamber,
   wherein said device further comprises:
   (A) a bag of supple plastic material forming said collecting chamber;
   (B) a rigid lower vessel to contain the said bag, wherein the space between the said bag and the walls of said vessel form an air jacket;
   (C) a multi-way valve comprising a means defining a plurality of passages connected to said positive pressure source, to said negative pressure source, to said filtering chamber, to said supple plastic bag and to said air jacket, said multi-way valve having a first position whereby the source of negative pressure is connected to said supple bag and said supple bag is connected to the filtering chamber thereby drawing blood from the suction means to the filtering chamber and from there to the supple bag, said valve having a second position whereby the source of positive pressure is connected to the air jacket, and at the same time the supple bag is isolated and closed, whereby the pressure in the air jacket is transmitted to the supple bag causing the blood to be delivered to the back-transfusion means.

2. The device of claim 1, wherein the filtering chamber is formed by a rigid upper vessel surmounting said rigid lower vessel, said upper vessel being of generally truncated form comprising a funnel-shaped bottom having a passage communicating with said multi-way valve and wherein said rigid upper vessel comprises a lid provided with handles for suspension purposes.

3. The device of claim 2, wherein said lid of the said rigid upper vessel comprises a bellows provided in its upper part with a stopper of tight and supple material capable of being pierced by a syringe containing anti-coagulant products, and the bellows being in communication with a spray nozzle within said upper vessel, whereby maneuvering said bellows produces a spray of said anti-coagulant in the atmosphere of said filtering chamber.

4. The device of claim 2, wherein the upper vessel forming the filtering chamber is connected to the lower vessel by a substantially circular belt containing the multi-way valve in the form of a tubular pipe, constituting the valve body provided with passages, a first passage to communicate with the filtering chamber, a second passage to communicate with the supple bag forming the collecting chamber, a third and a fourth passage to communicate with said air jacket, a fifth passage to communicate with the inside of the supple bag, a sixth passage to communicate with the source of negative pressure, and a seventh passage to communicate with the source of positive pressure, and said tubular pipe includes an internal rotatable key with a first channel connecting said first and second passages in a first position in the key, a second channel connecting said third and fifth passages for said first position of the key, a third channel connecting the fourth passage to the sixth passage for said first position of the key, said third channel connecting the fourth passage and the seventh passage in a second position of the key.

5. The device of claim 1, wherein the filtering beds inside said filtering chamber are formed by a plurality of superposed filtering cloths with different mesh sizes decreasing from top to bottom within the filtering chamber and each of said filtering cloths is supported by a peripheral ring, the diameter of which decreases from the top towards the bottom, thus allowing the rings to be force-fitted against the truncated walls of the said rigid upper vessel and the filtering cloth in its central part is of conical form, the apex of which is oriented upwardly, the peripheral part of said upper filtering cloths is in the form of an inverted conical frustum and said upper filtering cloth comprises on its upper surface upwardly extending vertical points for retention of clots conveyed in the blood.

6. The device of claim 1, wherein the second source of anticoagulant is in the form of a substantially spherical pouch contained in the interior of said supple bag and filled with anticoagulant products, the walls of said pouch being formed by a membrane of elastically deformable material and traversed by a multiplicity of pores allowing the anticoagulant to be exuded outwardly and mixed with the blood, said elastically deformable pouch being adapted to expand when the air jacket and the bag contained therein are in communication with the source of negative pressure, thus causing the opening of the pores.

7. A device according to claim 1, wherein said suction means is a suction nozzle connected to the filtering chamber via a connecting tube in communication, in the vicinity of said suction nozzle, with a source of an active product in the liquid state to be injected into said tube immediately after the blood enters said suction nozzle, wherein said active product is selected from the group consisting of an anticoagulant, isotonic saline solution, aqueous emulsions of macro-molecules of the DEXTRAN type and artificial foods.

8. A device for recovering and infusing blood from a patient comprising:
(a) means for suctioning blood from a patient;
(b) a first blood-receiving receptacle defining a filter chamber comprising a plurality of filter beds, means connected to said suction means for transferring blood to said first receptacle, and first means to introduce an anticoagulant to said filter chamber;
(c) a second blood receiving receptacle connected to the first receptacle by a hollow conduit, said second receptacle including a return means to infuse filtered blood to said patient;
(d) a collapsible blood collecting bag disposed in said second receptacle and connected to said hollow conduit communicating with said first receptacle, said collecting bag further communicating with said return means, said bag defining an air jacket between the wall of said second receptacle and said bag, said bag further including means to communicate with said air jacket;
(e) means for selectively introducing a negative pressure to said air jacket whereby a negative pressure is created in said bag and said first receptacle to suction blood from said patient;
(f) valve means to selectively interrupt said negative pressure and said communication of the interior of said bag to said air jacket and to close said conduit communicating said bag with said first chamber; and
(g) means to selectively introduce a positive pressure to the air jacket to compress said bag when said negative pressure is interrupted and said conduit is closed whereby blood within the bag is expelled from the bag through said return means.

9. The device of claim 8 wherein said second vessel further includes a filter means between said bag and return means.

10. The device of claim 8 wherein said valve means includes a first port connecting said hollow conduit of the second receptacle and the interior of the bag to said first receptacle, a second port connecting the air jacket to the interior of said bag, a third port connecting said air jacket to a negative pressure means and a fourth port connecting said jacket to a positive pressure means, said valve means being rotatable from a first position wherein said first, second and third ports are open whereby a negative pressure is introduced to said air jacket, the interior of the bag and the first receptacle, said valve means further being rotatable to a second position whereby said first, second and third ports are closed and said fourth port is open whereby a positive pressure is introduced to said air jacket.

11. The device of claim 8 wherein said first receptacle has as substantially truncated conical shape having converging side walls and a funnel-shaped bottom portion.

12. The device of claim 11 wherein said filtering beds in said filtering chamber comprise a plurality of superposed, spaced-apart filtering means of decreasing diameter and decreasing mesh size, whereby said filtering means engage the converging side walls of the first receptacle at different locations.

13. The device of claim 12 wherein said filtering means are a substantially conical shape and are disposed in the first receptacle with their apexes directed upwardly.

14. The device of claim 8 wherein said first receptacle includes a lid supporting said first means to introduce said anticoagulant, said means to introduce the anticoagulant comprising a bellows having means to receive said anticoagulant from a source, said bellows being in communication with a spray nozzle to delivery said anticoagulant within said filter chamber.

15. The device of claim 8 further comprising a second means to deliver an anticoagulant within said bag comprising a substantially spherical pouch having an expandable porous membrane capable of releasing said anticoagulant when the membrane is expanded and resisting release of the anticoagulant when in a contracted state.

16. The device of claim 8 wherein said filter chamber further includes a filter means having an upwardly extending conical-shaped apex wherein said filter has a substantially W-shaped cross-section and wherein the upper surface of said filter means includes a plurality of upwardly extending collection members for collecting clots in said blood.

17. A device for recovering and infusing blood from a patient comprising:
(a) a means for suctioning blood from a patient and means to return said blood to the patient;
(b) a first blood receiving vessel defining a filter chamber comprising a plurality of filter beds, means connected to said suction means for carrying blood to said first vessel, and first means to introduce anticoagulant to said filter chamber;

(c) a second blood receiving vessel defining a vacuum chamber and connected to said first vessel and said return means;

(d) a collapsible blood collecting bag disposed in said second vessel, the interior of said bag being in communication with said filter chamber, said vacuum chamber, and said return means, said bag being disposed in the second vessel whereby an air jacket is formed between the bag and the wall of the vessel;

(e) means for producing a negative pressure in communication with said second vessel and air jacket whereby a negative pressure is produced in said bag and first vessel to suction blood from said patient;

(f) means to produce pressure in said air jacket to compress said bag whereby blood is expelled from the bag to said return means; and (g) valve means disposed in said vacuum chamber to selectively interrupt communication of the air jacket with the interior of said bag and to interrupt communication of the interior of the bag with the filter chamber, and to selectively interrupt said positive pressure and negative pressure to the air jacket.

* * * * *